(12) United States Patent
Schmidt et al.

(10) Patent No.: US 6,613,511 B1
(45) Date of Patent: Sep. 2, 2003

(54) CHARACTERIZING DNA

(75) Inventors: Gunter Schmidt, Cambridge (GB); Andrew Hugin Thompson, Alloway (GB)

(73) Assignee: Xzillion GmbH & Co., Frankfurt (DE)

( * ) Notice: Subject to any disclaimer, the term of this patent is extended or adjusted under 35 U.S.C. 154(b) by 0 days.

(21) Appl. No.: 09/402,542

(22) PCT Filed: Apr. 20, 1998

(86) PCT No.: PCT/GB98/01134

§ 371 (c)(1),
(2), (4) Date: Dec. 29, 1999

(87) PCT Pub. No.: WO98/48047

PCT Pub. Date: Oct. 29, 1998

(30) Foreign Application Priority Data

Apr. 21, 1997 (GB) .............................. 9707980

(51) Int. Cl.⁷ ................................. C12Q 1/68
(52) U.S. Cl. .................. 435/6; 435/91.2; 536/24.3
(58) Field of Search ................. 435/6, 91.2; 536/24.3

(56) References Cited

U.S. PATENT DOCUMENTS

| 5,508,169 A | 4/1996 | Deugau et al. | |
|---|---|---|---|
| 5,681,726 A | 10/1997 | Hansen et al. | |
| 5,695,937 A | * 12/1997 | Kinzler et al. | 435/6 |
| 5,707,807 A | * 1/1998 | Kato | 435/6 |

FOREIGN PATENT DOCUMENTS

| EP | 0 735 144 A | 10/1996 |
|---|---|---|
| WO | WO 93/13220 | 7/1993 |
| WO | WO 95/04160 | 2/1995 |
| WO | WO 95/33073 | 12/1995 |
| WO | WO 98/10095 | 3/1998 |
| WO | WO 98/15652 | 4/1998 |
| WO | WO 98/31830 | 7/1998 |

OTHER PUBLICATIONS

Padgett et al. Gene, 168 (1996) 31–35.*
Kato, Nucleic Acids Research, vol. 23, No. 18, 1995 pp. 3685–3690.
Velculescu et al., Science, vol. 270, Oct. 20, 1995, pp. 484–487.

* cited by examiner

Primary Examiner—Jeffrey Fredman
Assistant Examiner—Juliet Einsmann
(74) Attorney, Agent, or Firm—Burns, Doane, Swecker & Mathis, L.L.P.

(57) ABSTRACT

The present invention is drawn to a method for characterizing cDNA, wherein said method produces a sequence signature having the following structure:

Adaptor Sequence-Restriction Site-Known Length-$N_w$-Second Known Length-$N_x$-Poly-A tail (Known Length).

25 Claims, 5 Drawing Sheets

STEP 1

STEP 2 ↓

STEP 3 ↓

STEP 4 ↓

CHARACTERIZING DNA

The present invention relates to a method for characterising DNA, especially cDNA, so that the DNA may be identified, for example, from a population of DNAs. The invention also relates to a method for assaying the DNA.

Analysis of complex nucleic acid populations is a common problem in many areas of molecular biology, nowhere more so than in the analysis of patterns of gene expression. Various methods have been developed to allow simultaneous analysis of entire mRNA populations, or their corresponding cDNA populations, to enable us to begin to understand patterns of gene expression in vivo.

Present methods, however, suffer from numerous drawbacks. The simplest methods such as 'subtractive cloning' allow crude comparative information about differences in gene expression between related cell types to be derived, although these methods have had moderate success in isolating rare cDNAs. Other methods such as 'differential display' and related 'molecular indexing' methods allow broader comparisons of gene expression between cell types but embodiments of these methods to date have been difficult to automate and are dependant on gel electrophoresis for analysis. Still more informative methods have arrived recently such as SAGE, Serial Analysis of Gene Expression, which give quantitative data on gene expression without prior knowledge and can readily and specifically identify cDNAs expressed in a given cell type but at the cost of excessive sequencing.

The method of "subtractive cloning" (Lee et al, Proc. Nat. Acad. Sci. USA 88, 2825–2829) allows identification of mRNAs, or rather, their corresponding cDNAs, that are differentially expressed in two related cell types. One can selectively eliminate cDNAs common to two related cell types by hybridising cDNAs from a library derived from one cell type to a large excess of mRNA from a related, but distinct cell type. mRNAs in the second cell type complementary to cDNAs from the first type will form double-stranded hybrids. Various enzymes exist which degrade such ds-hybrids allowing these to be eliminated thus enriching the remaining population in cDNAs unique to the first cell type.

The method of "differential display" (Laing and Pardee, Science 257, 967–971, 1992) sorts mRNAs using PCR primers to selectively amplify specific subsets of an mRNA population. An mRNA population is sub-divided into aliquots, each of which is primed with a series of "anchored" poly-T primers to effect reverse transcription with normalisation of the length of the poly-A tail. A set of redundant gene specific primers, of maybe 10 nucleotides or so are used to amplify the reverse strand. Typically a set of 30 such primers are used. In this way mRNAs are characterised by the length of their amplification products. The resultant amplified sub-populations can then be cloned for screening or sequencing or the fragments can simply be separated on a sequencing gel. Low copy number mRNAs are less likely to get lost in this sort of scheme in comparison with subtractive cloning, for example, and it is probably marginally more reproducible. Whilst this method is more general than subtractive cloning, time-consuming analysis is required. Unfortunately with these methods each cDNA may have multiple amplification products. Furthermore, the methods are not quantitative and comparative information can only be determined for relatively closely related cell types, e.g. diseased and normal forms of a particular tissue from the same organism.

The method of serial analysis of gene expression (Velcelescu et al., Science 270, 484–487, 1995) allows identification of mRNAs, or rather, their corresponding cDNAs that are expressed in a given cell type. It gives quantitative information about the levels of those cDNAs as well. The process involved isolating a signature 'tag' from every cDNA in a population using adaptors and type IIs restriction endonucleases. A tag is a sample of a cDNA sequence of a fixed number of nucleotides sufficient to uniquely identify that cDNA in the population. Tags are then ligated together and sequenced. The method gives quantitative data on gene expression and will readily identify novel cDNAs.

Methods involving hybridisation grids, chips and arrays are advantageous in that they avoid gel methods for sequencing and are quantitative. They can be performed entirely in solution, thus are readily automatable. Such arrays of oligonucleotides are a relatively novel approach to nucleic acid analysis, allowing mutation analysis, sequencing by hybridisation and mRNA expression analysis. For gene expression analysis oligonucleotides complementary to and unique to known RNAs can be arrayed on a solid phase support such as a glass slide or membrane. Labelled cDNAs or mRNA are hybridised to the array. The appearance of labelled nucleic acid immobilised at a specific locus on the array is indicative of the presence of the corresponding mRNA to which the oligonucleotide at that locus is complementary. Methods of construction of such arrays have been developed, (see for example: A. C. Pease et al. Proc. Natl. Acad. Sci. USA. 91, 5022–5026, 1994; U. Maskos and E. M. Southern, Nucleic Acids Research 21, 2269–2270, 1993; E. M. Southern et al., Nucleic Acids Research 22, 1368–1373, 1994) and further methods are envisaged. Unfortunately, these methods require that the sequence of RNAs be known prior to construction of the array. This means that this approach is not applicable to organisms for which little or no information is known.

Immobilisation can be followed by partial sequencing of fragments by a single base method, e.g. using type IIs restriction endonucleases and adaptors. This particular approach is advocated by Brenner in PCT/US95/12678.

Arrays of oligonucleotides of N bp length can be employed. The array carries all $4^N$ possible oligonucleotides at specific points on the grid. Nucleic acids are hybridised as single strands to the array. Detection of hybridisation is achieved by fluorescently labelling each nucleic acid and determining from where on the grid the fluorescence arises, which determines the oligonucleotide to which the nucleic acid has bound. The fluorescent labels also give quantitative information about how much nucleic acid has hybridised to a given oligonucleotide. This information and knowledge of the relative quantities of individual nucleic acids should be sufficient to reconstruct the sequences and quantities of the hybridising population. This approach is advocated by Lehrach in numerous papers and Nucleic Acids Research 22, 3423 contains a recent discussion. A disadvantage of this approach is that the construction of large arrays of oligonucleotides is extremely technically demanding and expensive.

The method of "molecular indexing" (PCT/GB93/01452) uses populations of adaptor molecules to hybridise to the ambiguous sticky-ends generated by cleavage of a nucleic acid with a type IIs restriction endonuclease to categorise the cleavage fragments. Using specifically engineered adaptors one can specifically immobilise or amplify or clone specific subsets of fragments in a manner similar to differential display but achieving a greater degree of sorting and control. However, time-consuming analysis is required and the methods disclosed in this patent application are difficult and expensive to automate.

The method of Kato (Nucleic Acids Research 23, 3685–3690, 1995) exemplifies the above molecular indexing approach and effects cDNA population analysis by sorting terminal cDNA fragments into sub-populations followed by selective amplification of specific subsets of cDNA fragments. Sorting is effected by using type IIs restriction endonucleases and adaptors. The adaptors also carry primer sites which in conjunction with general poly-T primers allows selective amplification of terminal cDNA fragments as in differential display. It is possibly more precise than differential display in that it effects greater sorting: only about 100 cDNAs will be present in a given subset and sorting can be related to specific sequence features rather than using primers chosen by trial and error. The subsets can then be analysed by gel electrophoresis to separate the fragments by length and generate a profile of mRNAs in a tissue. This method is dependant on PCR amplification which distorts the frequencies of each cDNA present. Furthermore the methods of analysis used so far have been dependant on gel electrophoresis.

The Gene Profiling technology described in patent PCT/GB97/02403 provides a further method of molecular indexing for the analysis of patterns of gene expression in a cell by sampling each cDNA within the population of that cell. In one embodiment, the sampling system takes two samples of 4 bp from each cDNA in a population and determines their sequence with respect to a defined reference point. The methods of this invention are amenable to automation but require many steps to derive signature information.

EP-A-735144 discloses a method for characterising cDNA. An array of adaptors is used to identify a short sequence sample at the 5' terminus of a 3' terminal restriction fragment of a cDNA. The cDNA is generated by cleavage with a type IIS restriction endonuclease. The adaptors introduce a primer sequence into the terminus of the fragments. The sequence identifies the sticky end generated by the cleavage. The adaptored fragments are cleaved with a further type IIS restriction endonuclease and fragments are selectively amplified using the adaptor primer sequence and a poly-T primer. This process is used to resolve a population of terminal restriction fragements. The method allows further resolution by separating the fragments according to sequence length.

U.S. Pat. No. 5,508,169 discloses a population of adaptor molecules which may be hybridised and ligated to ambiguous sticky ends generated by cleavage of a nucleic acid with a type IIS restriction endonuclease. The adaptors are disclosed in relation to the construction of a "universal endonuclease".

All of the above methods are relatively laborious and rely upon sequencing by traditional gel methods. Moreover, the methods require amplification by PCR, which is prone to produce artefacts.

It is an object of this invention to provide a method of gene expression profiling that is amenable to high throughput and automation which has great sensitivity. In this way should be possible to avoid the need for exponential amplification of cDNAs which distorts the frequencies of the cDNAs which is essential information in interpreting changes in gene expression patterns between different states of a given tissue and between different tissues of the same organism which have differentiated differently. This invention provides methods to derive a signature for each cDNA in a library which require fewer steps hence reducing sample loss and distortion of quantities of each mRNA by exploiting restriction fragment length polymorphisms to provide information about cDNAs.

Accordingly, the present invention provides a method for characterising cDNA, which comprises:

(a) exposing a sample comprising a population of one or more cDNAs or fragments thereof to a cleavage agent which recognises a predetermined sequence and cuts at a reference site at a known displacement from the predetermined sequence proximal to an end of each cDNA or fragment thereof so as to generate a population of terminal fragments;

(b) ligating to each reference site an adaptor oligonucleotide which comprises a recognition site for a sampling cleavage agent;

(c) exposing the population of terminal fragments to a sampling cleavage agent which binds to the recognition site and cuts at a sampling site of known displacement from the recognition site so as to generate in each terminal fragment a sticky end sequence of a predetermined length of up to 6 bases, preferably 3 to 5 bases, and of unknown sequence;

(d) separating the population of terminal fragments into sub-populations according to sequence length; and (e) determining each sticky end sequence.

It is not necessary to sequence an entire cDNA to identify uniquely its presence; only a short 'signature' of a few base pairs should be sufficient to identify uniquely all cDNAs, given, for example, a total cDNA population of about 80 000 in the human genome. Given also that in the next few years the entire human genome will have been sequenced, it should be possible to use such signatures derived by this process to acquire the entire sequence of the original cDNAs from a sequence database. With the incomplete database that already exists, signatures that return no sequence from the database will probably be novel and this process will readily allow them to be isolated for complete sequencing.

The cleavage agent is preferably a type II restriction endonuclease. In this case the reference site will contain the predetermined sequence (i.e. the known displacement will be zero) Alternatively, a type IIs restriction endonuclease or a chemical agent coupled to an oligonucleotide may be used. A sticky end or a blunt end may be generated although a sticky end is preferred.

Preferably each terminal fragment has a poly A tail. This provides a useful method for identifying the terminal fragment using a poly-T primer for reverse transcription. Alternatively, the 5' cap of the cDNA may be targeted.

In more detail, the first aspect of the present invention is a method which comprises the steps of:

1) generating 'anchored' cDNA captured on a solid phase support at the poly-T terminus. The cDNA is preferably methylated;

2) cleaving the cDNA fragments with a type II restriction endonuclease, and washing away cleaved fragments. Preferably the type II restriction endonuclease generates a known sticky-end;

3) ligating double stranded adaptors to the restricted cDNAs. Preferably the adapters bear a single stranded overlap complementary to a known sticky end generated by the restriction endonuclease from step (2) above. The double stranded region of the adapter bears a recognition sequence for a type IIs restriction endonuclease;

4) contacting the adaptored cDNAs with a type IIs restriction endonuclease to cleave the adapters from the cDNAs leaving an ambiguous sticky end of a predetermined length;

5) ligating a set of double stranded adaptors to the restricted cDNAs. The set of adaptors preferably comprises adapters bearing all possible single base extensions complementary to the ambiguous sticky-end of predetermined length generated in step (4). The adapters further comprise a mass label, cleavably linked to the adapter at the 5' distal from the ligation site, that uniquely identifies the sequence of the overlap of each adapter in the set when analysed by mass spectrometry. Optionally, each adapter may additionally comprise a primer sequence, such that each adapter has a unique primer sequence which corresponds to its overlapping sticky-end;

6) preferably conditioning the captured cDNAs for mass spectrometry;

7) denaturing the free strand from the captured strand releasing it into solution. This strand should bear the mass-label;

8) analysing the mass labelled cDNA terminal restriction fragments by Capillary Electrophoresis Mass Spectrometry.

The second aspect of the present invention is a method which comprises the steps of:

1) generating 'anchored' cDNA captured on a solid phase support at the poly-T terminus. The cDNA is preferably methylated;

2) cleaving the cDNA fragments with a type II restriction endonuclease, and washing away cleaved fragments. Preferably the type II restriction endonuclease generates a known sticky-end;

3) ligating double stranded adaptors to the restricted cDNAs. Preferably the adapters bear a single stranded overlap complementary to a known sticky end generated by the restriction endonuclease from step (2) above. The double stranded region of the adapter bears a recognition sequence for a type IIs restriction endonuclease;

4) contacting the adaptored cDNAs with a type IIs restriction endonuclease to cleave the adapters from the cDNAs leaving an ambiguous sticky end of a predetermined length;

5) ligating a set of double stranded adaptors to the restricted cDNAs. The set of adaptors preferably comprises adapters bearing all possible single base extensions complementary to the ambiguous sticky-end of predetermined length generated in step (4). The adapters further comprise a mass label, cleavably linked to the adapter at the 5' distal from the ligation site, that uniquely identifies the sequence of the overlap of each adapter in the set when analysed by mass spectrometry. Optionally, each adapter may additionally comprise a primer sequence, such that each adapter has a unique primer sequence which corresponds to its overlapping sticky-end;

6) denaturing the free strand from the captured strand releasing it into solution. This strand should bear the mass label. The captured strands are thus rendered single stranded;

7) contacting the captured single stranded with mass labelled primers complementary to the primer sequence provided by the adapters. The mass label attached to each primer identifies the sticky-end of the adapter to which the primer is complementary. Primers are preferably non-complementary and have equalised melting temperatures and can thus be added simultaneously. Optionally a second primer or set of primers may be used. These may be the anchored primers used in the synthesis of cDNA or may be a primer complementary to a site provided 5' of the anchored poly-T sequence;

8) extending primers in correctly hybridised duplexes with a DNA polymerase in the presence nucleotide triphosphates. This may be an exponential amplification if a second primer or set of primers is used;

9) melting the extended labelled strands off the immobilised template;

10) preferably conditioning the captured cDNAs for mass spectrometry;

11) determining the length of each of the amplified fragments and determining the identity of each of the amplified fragments by detection of the label incorporated with its primer. This detection if preferably performed by capillary electrophoresis mass spectrometry.

PCT/GB98/00127 describes nucleic acid probes labelled with markers that are resolvable by mass spectrometry. Such mass labelled probes would permit the analysis described here to be performed very rapidly as a captured library of restriction fragments can be probed with a number of uniquely mass labelled primers simultaneously.

The construction of adaptor oligonucleotides is well known and details and reviews are available in numerous texts, including: Gait, M. J. editor, 'Oligonucleotide Synthesis: A Practical Approach', IRL Press, Oxford, 1990; Eckstein, editor, 'Oligonucleotides and Analogues: A Practical Approach', IRL Press, Oxford, 1991; Kricka, editor, 'Nonisotropic DNA Probe Techniques', Academic Press, San Diego, 1992; Haugland, 'Handbook of Fluorescent Probes and Research Chemicals', Molecular Probes, Inc., Eugene, 1992; Keller and Manack, 'DNA Probes, 2nd Edition', Stockton Press, New York, 1993; and Kessler, editor, 'Nonradioactive Labeling and Detection of Biomolecules', Springer-Verlag, Berlin, 1992.

Conditions for using such adaptors are also well known. Details on the effects of hybridisation conditions for nucleic acid probes are available, for example, in any one of the following texts: Wetmur, Critical Reviews in Biochemistry and Molecular Biology, 26, 227–259, 1991; Sambrook et al, 'Molecular Cloning: A Laboratory Manual, 2nd Edition', Cold Spring Harbour Laboratory, New York, 1989; and Hames, B. D., Higgins, S. J., 'Nucleic Acid Hybridisation: A Practical Approach', IRL Press, Oxford, 1988.

Likewise, ligation of adaptors is well known and chemical methods of ligation are discussed, for example, in Ferris et al, Nucleosides and Nucleotides 8, 407–414, 1989; and Shabarova et al, Nucleic Acids Research 19, 4247–4251, 1991.

Preferably, enzymatic ligation would be used and preferred ligases are T4 DNA ligase, T7 DNA ligase, E. coli DNA ligase, Taq ligase, Pfu ligase, and Tth ligase. Details of such ligases are found, for example, in: Lehman, Science 186, 790–797, 1974; and Engler et al, 'DNA Ligases', pg 3–30 in Boyer, editor, 'The Enzymes, Vol 15B', Academic Press, New York, 1982. Protocols for the use of such ligases can be found in: Sambrook et al, cited above; Barany, PCR Methods and Applications, 1: 5–16, 1991; and Marsh et al, Strategies 5, 73–76, 1992.

One potential problem with the use of adaptors is to ensure that hybridisation of probes is accurate. There are major differences between the stability of short oligonucleotide duplexes containing all Watson-Crick base pairs. For example, duplexes comprising only adenine and thymine are unstable relative to duplexes of guanine and cytosine only. These differences in stability can present problems when trying to hybridise mixtures of short oligonucleotides (e.g. 4 mers) to complementary target DNA. Low temperatures are needed to hybridise A-T rich sequences but at these temperatures G-C rich sequences will hybridise to sequences that are not fully complementary. This means that some mismatches may happen and specificity can be lost for the G-C rich sequences. At higher temperatures G-C rich sequences will hybridise specifically but A-T rich sequences will not hybridise.

In order to normalise these effects modifications can be made to the Watson-Crick bases. The following are examples but they are not limiting:

The adenine analogue 2,6-diaminopurine forms three hydrogen bonds to thymine rather than two and therefore forms more stable base pairs.

The thymine analogue 5-propynyl dU forms more stable base pairs with adenine.

The guanine analogue hypoxanthine forms two hydrogen bonds with cytosine rather than three and therefore forms less stable base pairs.

These and other possible modifications should make it possible to compress the temperature range at which random mixtures of short nucleotides can hybridise specifically to their complementary sequences.

Preferably, the sampling cleavage agent comprises a type IIs restriction endonculease. Type IIs restriction endonucleases, the 'sampling endonucleases', have the property that they recognise and bind to a specific sequence within a target DNA molecule, but they cut at a defined distance away from that sequence generating single-stranded sticky-ends of known length but unknown sequence at the cleavage termini of the restriction products.

For example, the enzyme fok1, generates an ambiguous (i.e. unknown) sticky-end of 4 bp, 9 bp downstream of its recognition sequence. This ambiguous sticky-end could thus be one of 256 possible 4 bp oligonucleotides (see FIG. 1). Numerous other type IIs restriction endonucleases exist and could be used for this process as discussed below in section on restriction endonucleases. Their binding site can be provided by the adaptors used as shown in FIG. 2, for example.

Numerous type IIs restriction endonucleases exist and could be used as sampling enzymes for this process. Table 1 below gives a list of examples but is by no means comprehensive. A literary review of restriction endonucleases can be found in Roberts, R., J. Nucl. Acids Res. 18, 2351–2365, 1988. New enzymes are discovered at an increasing rate and more up to date listings are recorded in specialist databases such as REBase which is readily accessible on the internet using software packages such as Netscape or Mosaic. REBase lists all restriction enzymes as they are discovered and is updated regularly, moreover it lists recognition sequences and isoschizomers of each enzyme and manufacturers and suppliers. The spacing of recognition sites for a given enzyme within an adaptor can be tailored according to requirements and the enzyme's cutting behaviour. (See FIG. 2 above).

TABLE 1

Some typical type IIs restriction endonucleases

| Enzyme Name | Recognition sequence | Cutting site |
|---|---|---|
| Fok1 | GGATG | 9/13 |
| BstFs1 | GGATG | 2/0 |
| SfaNI | GCATC | 5/9 |
| HgaI | GACGC | 5/10 |
| BbvI | GCAGC | 8/12 |

The requirement of the process is the generation of ambiguous sticky-ends at the termini of the nucleic acids being analysed. This could also be achieved by controlled use of 5' to 3' exonucleases. Clearly any method that achieves the creation of such sticky-ends will suffice for the process.

Similarly the low stringency restriction endonuclease is necessary only to cleave each cDNA once, preferably leaving sticky-ends. Any means, however, of cleaving the immobilised nucleic acid would suffice for this invention. Site specific chemical cleavage has been reported in Chu, B. C. F. and Orgel, L. E., Proc. Natl. Acad. Sci. USA, 1985, 963–967. Use of a non-specific nuclease to generate blunt ended fragments might also be used. Preferably, though, a type II restriction endonuclease would be used, chosen for accuracy of recognition of its site, maximal processivity and cheap and ready availability.

Step (d) of separating the population of terminal fragments may be achieved by capillary electrophoresis, HPLC or gel electrophoresis. Capillary electrophoresis is preferred, particularly because this can be coupled directly to a mass spectrometer.

In step (e), each unknown sticky end sequence may be determined by:

(i) probing with an array of labelled hybridisation probes, the array containing all possible base sequences of the predetermined length;

(ii) ligating those probes which hybridised to the sticky end sequences; and (iii) determining which probes be ligated by identification and preferably quantification of the labels.

In one embodiment the array comprises a plurality of sub-arrays which together contain all the possible base sequences, and wherein each sub-array is contacted with the sticky end sequences Unligated probes are removed and these steps are repeated in a cycle so that all of the sub-arrays contact the sticky end sequences. In this way, the array of hybridisation probes is presented to the sticky end sequences in stages. For example, where the predetermined length of base sequence is 4 and the total number of possible base sequences is 256 ($4^4$), cross-hybridisation between complementary 4-mers in the array can be avoided by contacting the population of sticky end sequences with a first sub-array of 128 probes and, after removing all unligated probes, contacting with a second sub-array of 128 probes.

The labels are preferably mass labels such as those in accordance with GB 9700746.2 filed on Jan. 15th 1997.

Preferably, the present invention uses an array of hybridisation probes, each of which comprises a mass label linked to a known base sequence of predetermined length, wherein each mass label of the array, optionally together with the known base sequence, is relatable to that base sequence by mass spectrometry. Preferably, each of the hybridisation probes comprises a mass label cleavably linked to a known base sequence of predetermined length, wherein each mass label of the array, when released from its respective base sequence, is relatable to that base sequence by mass spectrometry, typically by its mass/charge ratio which is preferably uniquely identifiable in relation to every other mass label in the array.

In a further aspect, the present invention provides a method for identifying cDNA in a sample. The method comprises characterising cDNA as described above so as to obtain the fragment lengths, the sequences and relative positions of the reference site and sticky-ends and comparing those fragment lengths, sequences and relative positions with the sequences and relative positions of the reference site and sticky-ends of known cDNAs, such as those available from DNA databases, in order to identify the or each cDNA in the sample. This method can be used to identify a single cDNA or a population of cDNAs.

In a further aspect, the present invention provides a method for assaying for one or more specific cDNAs in a sample. This assay method comprises performing a method of characterising cDNA as described above, wherein the reference site and fragment lengths are predetermined, and each sticky-end sequence is determined by assay of a predetermined sticky-end sequence.

The invention will now be described in further detail by way of example only, with reference to the accompanying drawings, in which.

Figure 1:
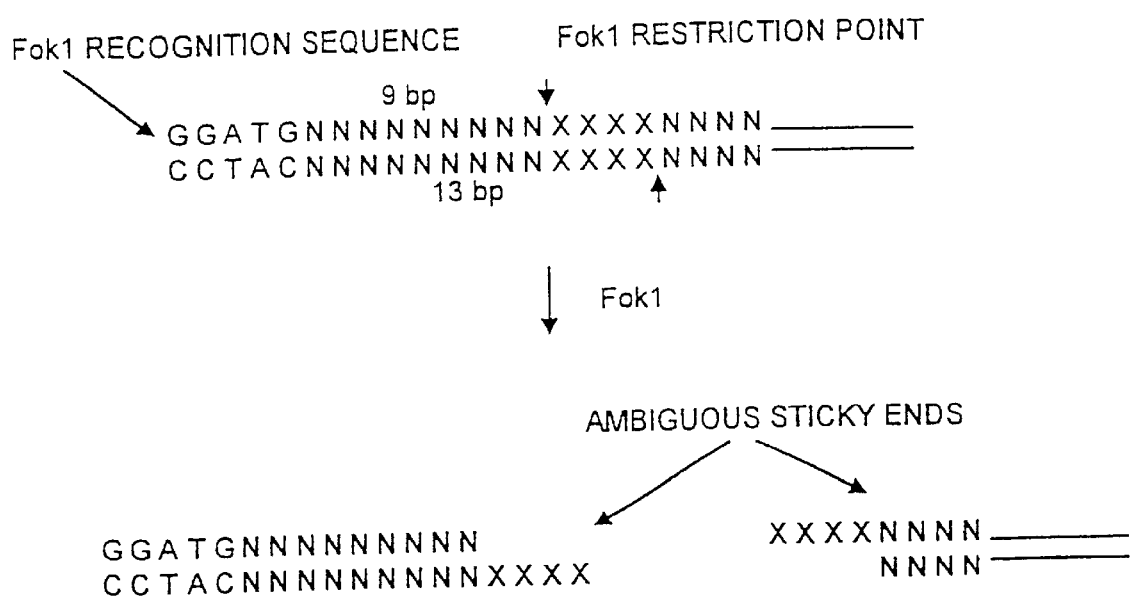
FIG. 1 shows the restriction behaviour of fok1.
Figure 2:
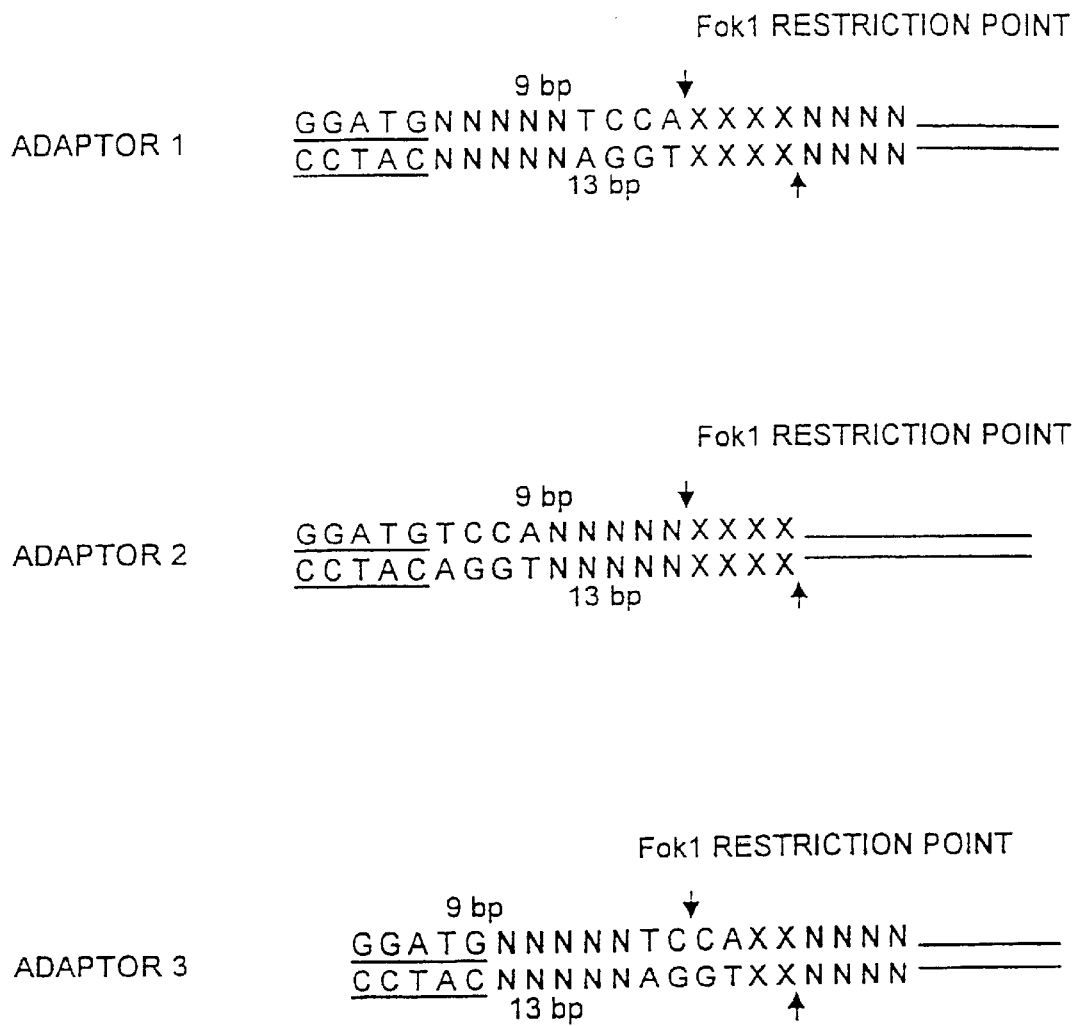
FIG. 2 shows the cutting behaviour of adaptor oligonucleotides.
Figure 3A:
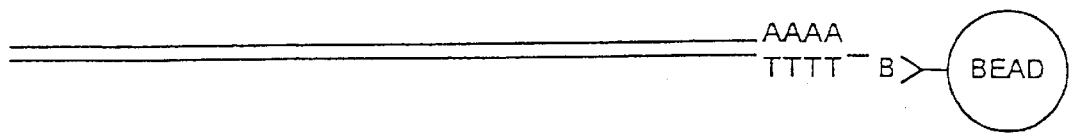
Figure 3A:
Figure 3A:
Figure 3A:
Figure 3B:
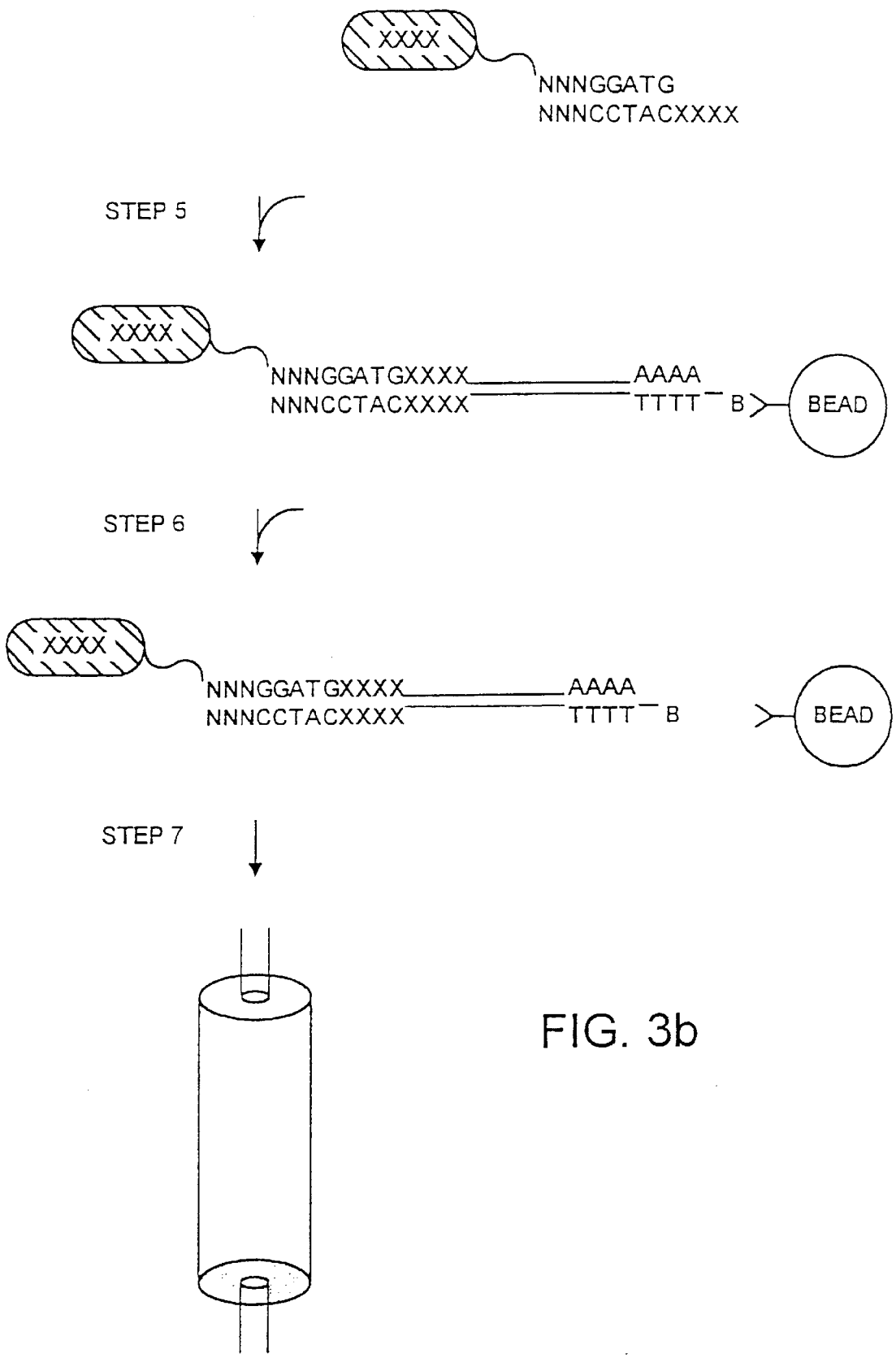
Figure 3C:
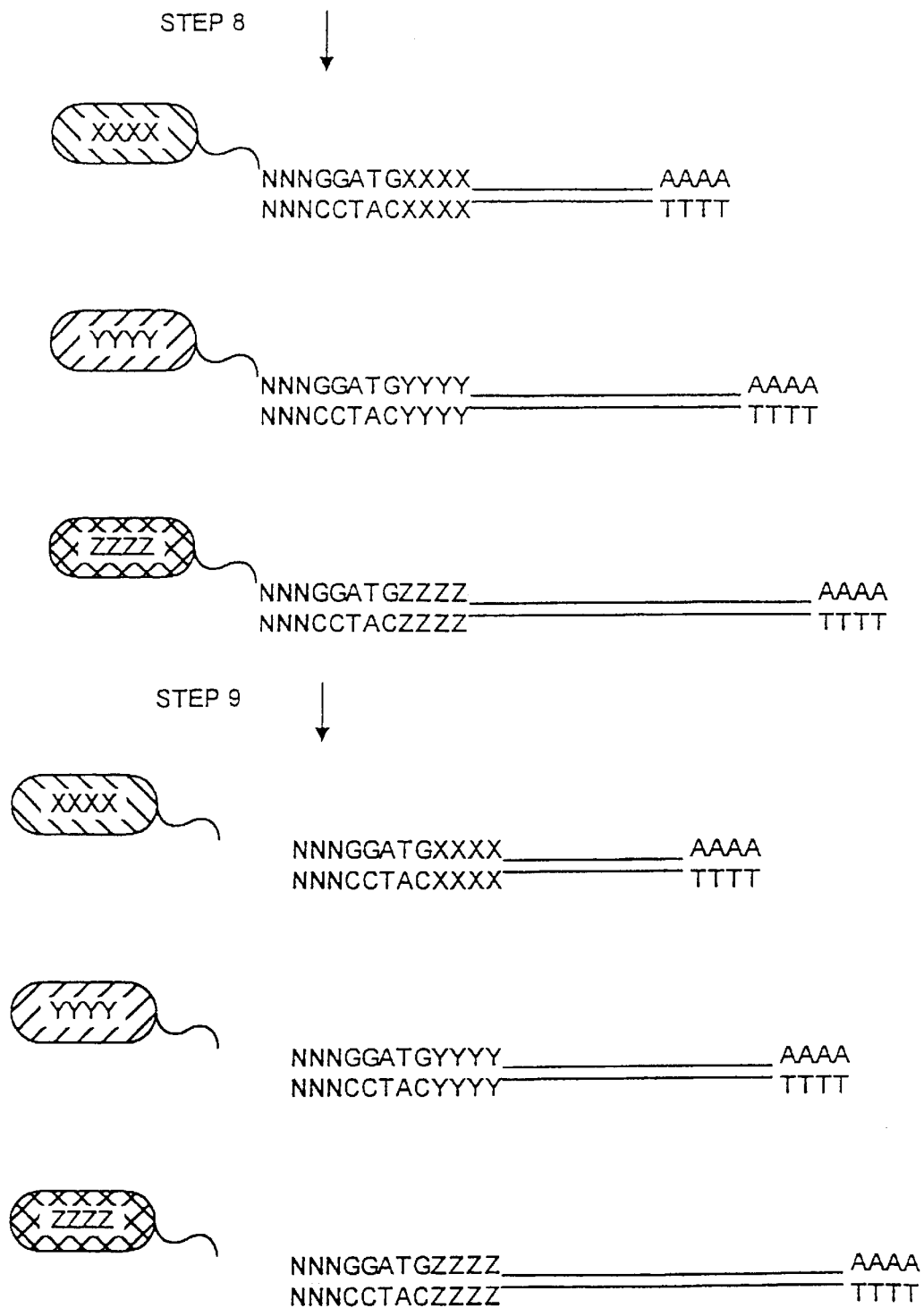

FIGS. 3a–c show a preferred method of characterising cDNA according to the present invention. In step 1 cDNA is generated on a solid phase support. In step 2 retained poly A carrying cDNAs are treated with "reference endonuclease" and cleaved fragments are washed away. In step 3 an adaptor is added with a sticky-end complementary to the "reference enzyme" sticky-end and carrying a binding site for the "sampling endonuclease". The "sampling enzyme" is added in step 4. In step 5, adaptors are added with sticky-ends complementary to all possible 4-base sticky-ends. These adaptors will also carry a label (preferably a mass label) to identify the sequence of the ambiguous sticky-end. Step 6 involves the release of the terminal restriction fragment from the solid phase support. In step 7, the liquid phase into which signature fragments have been released is removed and loaded into a microcapillary to separate fragments by length. In step 8, the capillaries are eluted and bands eluted from the capillary represent fragments of the same length. These can be identified by their label which is cleaved before the fragments enter the mass spectrometer. In step 9, the cleaved mass labels and signature fragments are injected preferably into an electrospray mass spectrometer for analysis. The charge of the label can be designed to be the opposite of the polynucleotide fragment. If it is negative then the labels can be analysed by positive ion mass spectrometry and vice versa. Preferably the charge on the fragment is positive and negative ion mass spectrometry is employed.

The Gene Profiling technology described in GB9618544.2 provides a method for the analysis of patterns of gene expression in a cell by sampling each cDNA within the population of that cell. In one embodiment, two samples of 4 bp are taken from each cDNA in a population and their sequence is determined with respect to a defined reference point.

The present invention is a simplification of that technology. Due to the way that cDNAs are prepared one can expect all cDNAs to be terminated with a short poly-A tail of fixed length. In most cDNA preparations the RNA is reverse-transcribed using a primer with about 18 deoxythymidine residues with one of the three other bases at the 5' end. This antisense strand of DNA is then made double-stranded using a second primer whose sequence is designed to bind within a coding sequence or is aided at the 5' terminus of the antisense strand. These will thus have reproducible lengths.

It is possible to use the length of poly-A bearing terminal cDNA restriction fragments to categorise every cDNA in a population into restriction fragment length subsets. With a short signature of about 4 bp from a known offset from the restriction site, one can sort each restriction fragment length set into a further 256 subsets. The distribution of fragment lengths will be determined by the restriction endonuclease used but as long as the variance of the length distribution varies by between 200 and 500 bases, it should be possible to identify substantially every cDNA in a population as this would generate in total between 75 000 and 125 000 signatures.

To generate these signatures, each cDNA in a population is immobilised and may be cleaved with an ordinary type II restriction endonuclease. An adaptor is ligated to the resulting known sticky-end. The adaptor is designed to carry the binding. site for a type IIs restriction endonuclease. These enzymes bind their target sequence but cleave the underlying DNA at a defined number of bases away from the binding site. Certain of these enzymes produce a staggered cut, fok1 for example will generate an ambiguous 4 bp sticky-end. If a population of cDNAs is treated with such an enzyme the sticky end will be exposed at the adaptored terminus of each cDNA in the population. A family of adaptor molecules is used to probe those 4 exposed bases. With a 4 bp ambiguous sticky-end there are 256 possible candidates. To identify the probes, they are tagged with mass labels using a photocleavable linker, so that each of the 256 possible 4 bp adaptors is identified by a label with a unique mass. These labels are optimised for good performance in a mass spectrometer as discussed in GB9700746.2. One is left with a population of fragments with varying lengths according to where the ordinary type II restriction endonuclease cut them and with one of 256 possible mass labelled adaptors at the 5' terminus of the cDNA.

Such a system could be made compatible with Liquid Chromatography Mass Spectrometry (LCMS). The gene profiling process operates in a two stage process, separation of restriction fragments by length followed by analysis of the mass labels ligated to the termini of the cDNA fragments. The separation by length could be achieved using capillary electrophoresis as the liquid chromatography stage feeding directly into at electrospray mass spectrometer. Between the capillary and the mass spectrometer one can also detect 'bands' of fragments of a given length by absorbance measurements. Between the capillary and the mass spectrometer the labels would also have to pass through a photocleavage stage to release all the mass labels from their restriction fragments. One would then identify for each restriction fragment length band from the capillary electrophoresis separation the quantity of each mass label present in that band. This would subsort every group with a distinct fragment length into 256 subsets.

To be able to uniquely identify each of the estimated 100 000 genes one will need to be able to resolve cDNAs into at least as many subsets. A recognition sequence between 4 or 5 bp will appear roughly every 256 or 1024 bases respectively. Further resolution could be achieve by using restriction enzymes th at cut more rarely or by using combinations of enzymes.

Preparation of cDNA

The methods of this invention entail isolating a terminal restriction fragment from each cDNA in a library, from either the 3' or the 5' terminus, from which a short window of sequence is determined at a known location with respect to the terminal restriction site. In order to exploit fragment length information to categorise a cDNA population, the cDNA is prepared with 'anchored primers' which ensure that all cDNAs are terminated with a short poly-A tail of fixed length. In an 'anchored primer' cDNA preparation, poly-A carrying mRNAs are captured and primed using an oligonucleotide of about 18 deoxythymidine residues with one of the three remaining bases at the 3' end to anchor the primer at the end of the poly-A tract. The primed mRNA is then copied into DNA with reverse transcriptase. This generates an mRNA/DNA hybrid duplex. The complementary strand of DNA thus synthesised can then made double-stranded. Various methods are known in the art to effect the synthesis of the second strand. DNAse I can be used to nick the mRNA/DNA duplex providing 3' hydroxyls for a DNA polymerase to synthesise from. Alternatively the second strand synthesis may be effected using a second primer whose sequence is designed to bind within a coding sequence or is aimed at the 5' terminus of the complementary strand or which introduces a restriction site into the cDNA. This approach requires the degradation of the mRNA in the hybrid duplex. This may be effected by treatment with an alkali, by thermal denaturation or by treatment with RNAse H. A further method is the use of terminal transferase. If the 'anchored primer' is biotinylated, it can be captured onto an avidinated surface, or if it is already covalently linked to a solid phase substrate then after synthesis of the complementary strand the reverse transcriptase and nucleotides can be readily washed away. Buffer containing terminal transferase and one type of nucleotide triphosphate can then be added which will add an arbitrary number of nucleotides of that type to the 3' hydroxyls of the duplex. This generates a known sequence at the terminus of the cDNA, preferably poly-cytosine or poly-guanine. After removing the RNA, by thermal denaturation or alkali degradation, the reverse strand can be synthesised by providing an oligonucleotide primer complementary to the terminal transferase generated terminal sequence. This primer can overlap into the unknown sequence beyond that provided by terminal transferase allowing differential amplification of subsets of the cDNA library. Many other methods are known and any method that allows the generation of the complementary strand can be used with the methods of this invention but preferably the method chosen should not entail loss of any portion of the library.

In addition to normalising the length of poly-A tail of RNA species, the anchoring base on the poly-T primers can be used in the preparation of the cDNAs to sort the cDNA population into subsets. If a 1 base overlap is used the cDNA population can be sorted into 3 subsets. With 2 bases 12 subsets are possible and similarly with a 3 base overlap 48 sets are possible. Preferably a 1 base overlap or a 3 base overlap is used. With a 1 base overlap, the mRNA extract from a tissue is subdivided into 3 pools and is contacted with one of the three possible anchoring primers in each pool separately from which cDNA is then reverse transcribed.

When the length of the poly-A tail is normalised as above it is possible to use the length of poly-A bearing terminal cDNA restriction fragments to categorise every cDNA in a population into restriction fragment length subsets. With a short signature of about 4 bp from a known position within the fragments it should be possible to uniquely identify the majority of cDNAs in a population. Those cDNAs that are not uniquely resolved are likely to fall into gene families whose sequences are closely related.

To determine signatures from 'anchored' cDNAs, each cDNA in a population is immobilised on a solid phase substrate. The cDNA is prepared as above by capturing the poly-A+ mRNAs with anchored poly-T primers, preferably with a single phase locking base at its 3' terminus. Additionally the anchored primers are biotinylated allowing the cDNAs to be immobilised onto an avidinated matrix. Alternatively the anchored primers can be covalently linked to the solid phase substrate. The phase locking base can be used to subdivide the sample into three separation populations for amplification if that is desired. The poly-T primer may additionally carry a primer sequence at its 5' terminus. The captured cDNAs generated are then cleaved with an ordinary type II restriction endonuclease. An adaptor is ligated to the resulting known sticky-end. The adaptor is designed to carry the binding site for a type IIs restriction endonuclease. These enzymes bind their target sequence but cleave the underlying DNA at a defined number of bases away from the binding site. Certain of these enzymes produce a staggered cut; the enzyme fok1 for example, will generate an ambiguous 4 bp sticky-end. If a population of cDNAs is treated with such an enzyme the sticky end will be exposed at the adaptored terminus of each cDNA in the population. A family of adaptor molecules is used to probe those 4 exposed bases. With a 4 bp ambiguous sticky-end there are 256 possible adaptors. To identify the adaptors, they are tagged with mass labels using a cleavable linker, so that each of the 256 possible 4 bp overlaps is identified by a label that is uniquely identifiable in a mass spectrometer. These labels are optimised for good performance in a mass spectrometer as discussed in patent PCT/GB98/00127. The result of the application of the above procedure is a population of fragments each of which has a characteristic length, according to where the ordinary type II restriction endonuclease cut it, and one of 256 possible mass labelled adaptors ligated to its 5' terminus.

Ensuring that no Type IIs Restriction Endonuclease Sites are Accessible at Internal Sites in the Target Nucleic Acid It is important to ensure no 'sequencing enzyme' binding sites are accessible or present in the template nucleic acid fragments prior to addition of adapters bearing the 'sequencing enzyme' binding site to the terminus of the molecule from which sequencing is to occur. Certain type IIs restriction endonucleases are sensitive to the methylation state of their recognition regions so to prevent unwanted sites being used by the sequencing endonuclease the target nucleic acid can be methylated prior to ligation of adapters bearing the sequencing endonuclease recognition site. Methylation can be achieved during the preparation of templates by use of 5-methyl cytosine triphosphates rather than cytosine triphosphates in any reverse transcription and amplification reactions. Use of unmethylated adapters would allow recognition sequences present in these to function but not those in the template.

Restriction of Nucleic Acids and Ligation of Adapters

In preferred embodiments the step of restriction of nucleic acids is coupled to the ligation of adapters (steps (2) and (3) in the aspects of the invention described above). Preferred restriction endonucleases for use with this invention cleave within their recognition sequence generating sticky-ends that do not encompass the whole recognition sequence. This allows adapters to be designed that bear sticky ends complementary to those generated by the preferred restriction endonuclease but which do not regenerate the recognition site of the preferred restriction endonuclease. This means that if the restriction reaction is performed in the presence of ligase and adapters, the ligation of restriction fragments to each other is reduced by continuous cleavage of these ligations whereas ligation of adapters is irreversible so the presence of adapters drives the restriction to completion and similarly the restriction endonuclease drives the ligation reaction to completion. This process ensures that a very high proportion of restriction fragments are ligated to adaptors. This is advantageous as ligation of adapters to restriction fragments is a relatively inefficient process. This is due to random ligation of restriction products to each other if these are phosphorylated.

In this embodiment the adapters used are preferably not phosphorylated at their 5' hydroxyl groups so that they cannot ligate to themselves.

Linear and Exponential Amplification of Tagged cDNAs

In the second aspect of this invention, each adaptor used to probe the ambiguous sticky ends generated by cleavage with a type IIs restriction endonuclease may additionally comprise a primer sequence. Each adaptor with a distinct sticky end is identified by a primer sequence that is distinct from the primer sequence associated with every other adapter. The design of sets of non-complementary tag sequences for this purpose is relatively simple. For a detailed discussion see Brenner, PCT/US95/12791. After generation of mass labelled adaptored cDNA fragments on the solid phase support, the free sense strand of the captured cDNA can be denatured from the solid phase support. The captured strand can be contacted with mass labelled primers complementary to the sequence of the tag sequence in the adapter. These may be extended by a polymerase with nucleotide triphosphates. Each cycle of denaturing and primer extension can be performed as many times as desired. If only the adapter primer sites are used, a linear amplification can be performed. This causes smaller distortion of cDNA quantitation than exponential amplification. If exponential amplification is desired then the poly-T oligos used to trap the mRNAs must carry a primer site as well. Exponential amplification may be desirable if small tissue samples must be analysed despite the potential for distortions of cDNA frequencies.

Capillary Electrophoresis Mass Spectrometry

The methods of this invention can exploit Liquid Chromatography Mass Spectrometry (LCMS), preferably capillary electrophoresis mass spectrometry. The gene profiling process operates in a two stage process, separation of restriction fragments by length followed by analysis of the mass labels ligated to the termini of the cDNA fragments. The separation by length could be achieved using capillary electrophoresis as the liquid chromatography stage feeding directly into an electrospray mass spectrometer. Between the capillary and the mass spectrometer the labels would have to pass through a cleavage stage to release all the mass labels from their restriction fragments. These features are discussed in PCT/GB98/00127. For each restriction fragment length band from the capillary electrophoresis separation, the quantity of each mass label present in that band is determined. This would subsort every group with a distinct fragment length into 256 subsets. If the phase locking base on the poly-T primers used in the preparation of the cDNAs is used to sort the cDNA population further then, the cDNA restriction fragments can be sorted into 768 subsets. Additional sub-sorting can be achieved using more than one base to lock the poly-T primer but the stringency of hybridisation is poorer the longer the probe sequence that is used. If the cDNA population is generated using the terminal transferase method described above, the cDNA population can be sorted using the known sequences at both termini to provide a platform for primers that extend into the unknown sequence adjacent to the known terminal sequences.

Bioinformatics

To be able to uniquely identify each of the estimated, 100 000 genes in the human genome, one will need to be able to resolve cDNAs into at least as many subsets. For practical purposes unique resolution is not strictly necessary but resolution into a large number of subsets is desirable as it makes it more likely that a cDNA can be unambiguously identified by sorting alone. A combination of sorting a cDNA library followed by probing to generate a short signature can allow an arbitrary degree of resolution of a cDNA library into subsets that are unique or nearly so. The signature can resolve a population into approximately 256 subsets if 4 base pair probe sequences are used at the adaptor sites. The anchored primer can resolve cDNAs into further subsets. With a 1 base overlap the anchored primers can generate 3 subsets. This gives an initial total cf 768 subsets. Restriction fragment lengths vary to a fairly wide degree giving further resolution that is statistically definable. Higher resolution could be achieved by using restriction enzymes that cut more rarely or by using combinations of enzymes. It might be desirable to perform two or more analyses per tissue using a different restriction endonuclease in each experiment to produce two or more sets of data for correlation. Each such experiment will generate a signature of the form shown below for each cDNA in a population:

Adaptor Sequence—Restriction Site—Known Length—$N_w$—Known Length—$N_x$—Poly-A tail (Known Length)—Optional Primer Sequence The features in bold are features of the source mRNA. N is base information where the subscripts w and x indicate the number of bases that are determined. The information generated comprises a digital signature that can be used to search a sequence database to identify the source gene.

What is claimed is:

1. A method for characterising cDNA, wherein said method produces a sequence signature having the following structure:

Adaptor Sequence-Restriction Site-Known Length-$N_w$-Second Known Length-$N_x$-Poly-A tail (Known Length), wherein N is base information and the subscripts w and x indicate the number of bases that are determined, which method comprises:

(a) exposing a sample comprising a population of one or more cDNAs or fragments thereof to a cleavage agent which recognizes a predetermined sequence and cuts at a reference site at a known displacement from the predetermined sequence proximal to the poly-A terminus an end of each cDNA or fragment thereof so as to generate a population of terminal fragments comprising the poly-A terminus;

(b) ligating to each reference site an adaptor oligonucleotide which comprises a recognition site for a sampling cleavage agent;

(c) exposing the population of terminal fragments comprising the poly-A terminus to a sampling cleavage agent which binds to the recognition site and cuts at a sampling site of known displacement from the recognition site so as to generate in each terminal fragment comprising the poly-A terminus a sticky end sequence of a predetermined length of up to 6 bases, and of unknown sequence;

(d) directly after completing step (c), separating the population of terminal fragments comprising the poly-A terminus into sub-populations according to sequence length, thereby determining the second known length of said sequence signature; and (e) determining each sticky end sequence.

2. A method according to claim 1, wherein each sticky end sequence has 3–5 bases.

3. The method according to claim 1, wherein the cleavage agent of step (a) is a type II restriction endonuclease.

4. A method according to claim 3, wherein the type II restriction endonuclease is selected such that the displacement from the reference site to the predetermined sequence is zero, and the adaptor oligonucleotide is selected such that upon ligation to the reference site the predetermined sequence is not regenerated.

5. A method according to claim 1, wherein each terminal fragment has a poly A tail.

6. A method according to claim 1, wherein the adaptors are ligated using enzymatic ligation.

7. A method according to claim 6, in which T4 DNA ligase, T7 DNA ligase, *E. coli* DNA ligase, Taq ligase, Pfu ligase, or Tth ligase is used.

8. A method according to claim 1, wherein the sampling cleavage agent comprises a type IIs restriction endonuclease.

9. A method according to claim 8, wherein the type IIs restriction endonuclease is the fok1, BstFsI, SfaNI, HgaI, or BbvI enzyme.

10. A method according to claim 1, wherein the population of terminal fragments is separated by capillary electrophoresis, HPLC or gel electrophoresis.

11. A method according to claim 1, wherein each unknown sticky end sequence is determined by a method comprising:
   i) probing with an array of labeled hybridization probes, the array containing all possible base sequences of the predetermined length;
   ii) ligating those probes which hybridized to the sticky end sequences; and
   iii) determining which probes are ligated by identification of the labels.

12. A method according to claim 11, wherein the array comprises a plurality of sub-arrays, and steps i), ii) and iii) are repeated for each sub-array.

13. A method according to claim 12, wherein the predetermined length of the sticky end sequences is 4 bases and the array comprises two sub-arrays, each sub-array containing 128 different probes, the probes in one sub array being complementary to the probes in the other sub-array.

14. A method according to any of claim 11, wherein the labels are cleavably attached to the hybridisation probes.

15. A method according to any of claim 11, wherein each label is specific to the base sequence of the probe to which it is attached.

16. A method according to any of claim 11, wherein the labels are mass labels.

17. A method according to any of claim 11, wherein each hybridisation probe is attached to a known double-stranded primer sequence specific to the base sequence of the probe, such that after hybridisation of the terminal fragments to the probes, each terminal fragment is attached to a primer sequence specific to that fragment, and wherein the terminal fragments are selectively amplified by performing PCR in the presence of one or more of said primer sequences.

18. A method according to any of claim 11, wherein prior to hybridisation, a terminal primer is introduced at the poly A tail of the cDNA, and wherein after hybridisation the terminal fragments are amplified by performing PCR in the presence of said terminal primer.

19. A method of claim 11, wherein said method further comprises the step of quantification of said labels.

20. A method according to claim 1, wherein the cDNA is synthesised using 5-methyl cytosine.

21. A method according to claim 1, wherein the cDNA is immobilised on a solid support.

22. A method of identifying cDNA in a sample, comprising characterising the cDNA by a method as defined in claim 1 and identifying said cDNA.

23. A method of assaying for one or more specific cDNAs in a sample, comprising characterizing the cDNA by a method as defined in claim 1 and assaying said cDNA for one or more specific cDNAs.

24. The method of claim 1, wherein said sequence signature further comprises 3' to the poly-A tail a primer sequence.

25. A method for characterizing cDNA, which method comprises:
   (a) exposing a sample comprising a population of one or more cDNAs or 3' terminal cDNA fragments of greater than 18 base pairs in length, including the poly-A terminus, to a cleavage agent which recognizes a predetermined sequence and cuts at a reference site at a known displacement from the predetermined sequence proximal to an end of each cDNA or 3' terminal cDNA fragments of greater than 18 base pairs in length so as to generate a population of terminal fragments;
   (b) ligating to each reference site an adaptor oligonucleotide which comprises a recognition site for a sampling cleavage agent;
   (c) exposing the population of terminal fragments to a sampling cleavage agent which binds to the recognition site and cuts at a sampling site of known displacement from the recognition site so as to generate in each terminal fragment a sticky end sequence of a predetermined length of up to 6 bases, and of unknown sequence;
   (d) separating the population of terminal fragments into sub-populations according to sequence length; and
   (e) determining each sticky end sequence.

* * * * *